United States Patent
Lynch et al.

(10) Patent No.: US 10,136,903 B2
(45) Date of Patent: Nov. 27, 2018

(54) TOURNIQUET AND METHOD THEREOF HAVING COMPLIANCE LOGGING AND ALERT FEATURES, AND A SYSTEM THEREOF

(71) Applicants: Patrick James Lynch, Los Angeles, CA (US); Trevor Alan Gililland, Los Angeles, CA (US); James Ryan Gielen, Los Angeles, CA (US)

(72) Inventors: Patrick James Lynch, Los Angeles, CA (US); Trevor Alan Gililland, Los Angeles, CA (US); James Ryan Gielen, Los Angeles, CA (US)

(73) Assignee: Patrick James Lynch, Hawthorne, CA (US)

( * ) Notice: Subject to any disclaimer, the term of this patent is extended or adjusted under 35 U.S.C. 154(b) by 283 days.

(21) Appl. No.: 15/082,865

(22) Filed: Mar. 28, 2016

(65) Prior Publication Data

US 2017/0273694 A1    Sep. 28, 2017

(51) Int. Cl.
  *G08B 21/00*  (2006.01)
  *A61B 17/17*  (2006.01)
  (Continued)

(52) U.S. Cl.
  CPC .......... *A61B 17/1732* (2013.01); *A61B 90/06* (2016.02); *A61B 90/08* (2016.02);
  (Continued)

(58) Field of Classification Search
  None
  See application file for complete search history.

(56) References Cited

U.S. PATENT DOCUMENTS 6,051,016 A    4/2000   Mesaros et al.
6,213,939 B1   4/2001   McEwen
(Continued)

FOREIGN PATENT DOCUMENTS

CN    203074798 U    7/2013
WO    2016011538 A1  1/2016

OTHER PUBLICATIONS

Magee, "MicroHealth Helps Patients Manage Chronic Illnesses", downloaded from Techcrunch (http://techcrunch.com/2015/08/05/yc-backed-microhealth-helps-patients-manage-chronic-illnesses). Retrieved on Mar. 28, 2016.

(Continued)

*Primary Examiner* — Adolf Dsouza

(57) ABSTRACT

A tourniquet, a method, and a system that can secure logging of compliance with an external communication apparatus and marry two segregated steps of infusing and logging. The tourniquet has a controller that monitors compliance based on signals received from various switches/sensors that indicate whether a clasp has been inserted in the buckle and thereafter whether a strap is applying pressure, and the clasp has been released within a predetermined time after the clasp has been inserted. The controller initiates communication with the external communication apparatus. Upon receiving a log successful communication from the external communication apparatus, the controller alerts the user that the logging was successful or compliance has been met.

15 Claims, 12 Drawing Sheets

(51) Int. Cl.
*A61B 90/00* (2016.01)
*G16H 40/63* (2018.01)
*A61B 17/00* (2006.01)

(52) U.S. Cl.
CPC .... *G16H 40/63* (2018.01); *A61B 2017/00115* (2013.01); *A61B 2017/00221* (2013.01); *A61B 2090/065* (2016.02); *A61B 2090/0808* (2016.02); *A61B 2090/0811* (2016.02)

(56) References Cited

U.S. PATENT DOCUMENTS

| | | | |
|---|---|---|---|
| 6,833,001 B1 | 12/2004 | Chao | |
| 7,955,352 B2 | 6/2011 | McEwen et al. | |
| 8,083,763 B2 | 12/2011 | McEwen et al. | |
| 8,103,241 B2 | 1/2012 | Young et al. | |
| 8,147,417 B2 | 4/2012 | Gavriely | |
| 8,147,533 B2 * | 4/2012 | Baxter | A61F 7/10 128/898 |
| 8,226,567 B2 | 7/2012 | Kojima et al. | |
| 8,721,678 B2 | 5/2014 | McEwen et al. | |
| 8,764,685 B2 | 7/2014 | Casey | |
| 9,149,280 B2 * | 10/2015 | Croushorn | A61B 17/135 |
| 9,456,826 B2 * | 10/2016 | Henderson | A61B 17/1325 |
| 2002/0094778 A1 | 7/2002 | Cannon et al. | |
| 2005/0113866 A1 * | 5/2005 | Heinz | A61B 17/1322 606/203 |
| 2006/0111639 A1 | 5/2006 | Su | |
| 2009/0118628 A1 | 5/2009 | Zhou et al. | |
| 2010/0211096 A1 | 8/2010 | McEwen et al. | |
| 2012/0179067 A1 | 7/2012 | Wekell | |
| 2013/0211445 A1 | 8/2013 | McEwen et al. | |
| 2014/0336697 A1 | 11/2014 | Masaki | |
| 2017/0112504 A1 | 4/2017 | McEwen et al. | |

OTHER PUBLICATIONS

International Search Report issued in Intl. Appln. No. PCT/US2017/24524 dated Jun. 19, 2017.

Written Opinion issued in Intl. Appln. No. PCT/US2017/24524 dated Jun. 19, 2017.

* cited by examiner

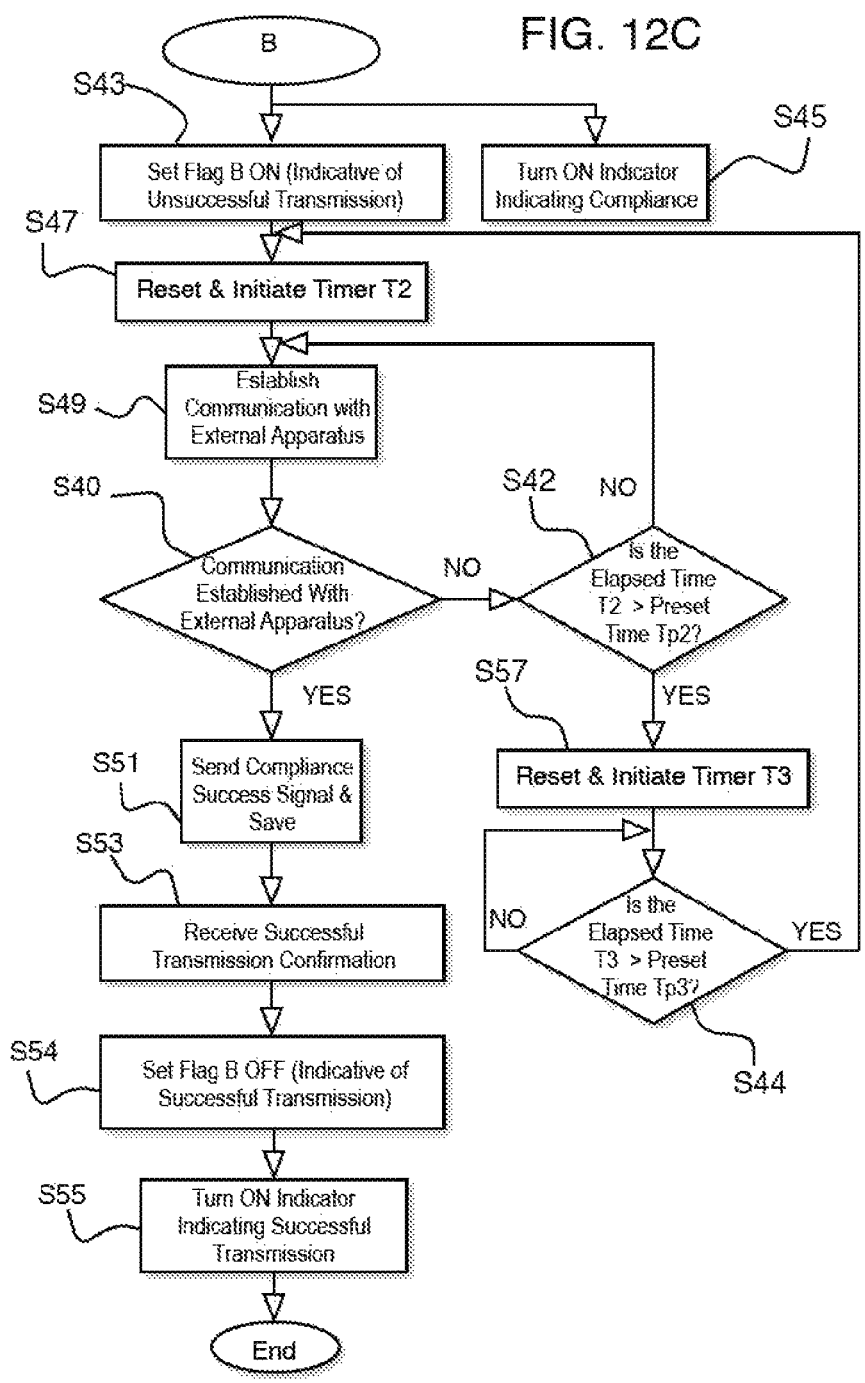

TOURNIQUET AND METHOD THEREOF HAVING COMPLIANCE LOGGING AND ALERT FEATURES, AND A SYSTEM THEREOF

BACKGROUND

The logging of tourniquet use is crucial. For patients self-managing hemophilia, which is a chronic disease that requires administering medicine intravenously on a routine basis from home or personal environment, an adequate record of administering medicine is absolutely necessary for the clinicians who prescribe the routine regimen, the pharmacies that fill the prescription, the homecare service providers that deliver medicine, the manufacturers that produce intravenous therapies, and the insurance companies that pay or reimburse. Similar considerations hold true for patients with other chronic conditions requiring the regular administration of injectable medications as well.

Since the implementation of the Affordable Card Act (ACA), the lifting of lifetime bans, and the inability for insurance companies to refuse service to people with pre-existing conditions, the need for accurate data collection from patients self-managing their chronic disease is more paramount than ever.

For the purpose of this description, a two-step process of (1) a patient's adherence to administering the intravenous therapy for the prescribed routine regimen and (2) the patient accurately logging the administering of the therapy of the prescribed routine regimen will be referred to as "compliance." One of the inventors lives with severe hemophilia A and intimately understands the importance of adhering to compliance. He has witnessed the ultimate penalty for non-compliance—unfortunate death of his sibling.

Studies have shown that the fewer the steps necessary to complete the infusion & logging process, the more likely the patient would be in compliance. Dr. Marc Lara (co-founder of the digital logging app MICROHEALTH) reported in an article *MicroHealth Helps Patients Manage Chronic Illnesses* by Christine Magee at the TECHCRUNCH website (http://techcrunch.com/2015/08/05/yc-backed-microhealth-helps-patients-manage-chronic-illnesses/) that patients who properly managed their factor intake, namely engaged in compliance, had a 40% reduction in the devastating bleeding episodes that plague people with hemophilia. With the banning of lifetime caps and discrimination based on pre-existing conditions under the ACA, insurance companies are actively seeking a system that can more accurately collect data to better understand, and ultimately reduce the cost: insurances companies spend about $300,000 annually on average for each hemophilic patient, with some patients costing insurance companies well over $1,000,000 annually.

Pharmaceutical manufacturers producing therapies for people with hemophilia regularly update the reconstitution system necessary to mix the powdered medicine with saline solution to reduce the steps required for a patient to self-administer the medicine. Technology companies also have developed digital applications with the capacity for pre-loading information to hasten the logging of the administered medicine.

Even though the applications can provide patients a way of logging and sharing logs with healthcare providers digitally, the two-step process necessary for compliance are still handled as two segregated actions, which can result in non-compliance, resulting in problems for the user, the healthcare provider, and the insurance reimbursement function.

The single biggest problem the population faces when it comes to data collection is compliance. There still remains a need to reduce the compliance steps of infusing and logging into a single step. The present development addresses this need.

SUMMARY

One aspect of the present development is a tourniquet, which uses a strap and a clasp connected to the strap, which is adjustably configured.

The tourniquet is communicable with an external communication apparatus that is configured to transmit a logging confirmation signal to the tourniquet confirming a successful logging of compliance.

The tourniquet includes a controller, an indicator connected to the controller, a first sensor connected to the controller, and a housing containing the controller and the first sensor. The housing has a receptacle configured to receive the clasp. The first sensor is configured to output a first signal when the clasp is inserted into the receptacle.

The controller includes a memory, a processor, and a first communication interface configured to communicate with the external communication apparatus. The processor is configured to execute a first determining task that determines whether the clasp has been inserted in the receptacle based on whether the first signal is received, a first communication task that controls the first communication interface to initiate communication with the external communication apparatus (which can be simple as transmitting an initiating signal thereto), upon the first determining task determining that the clasp has been inserted, and an alerting task that controls the indicator to alert a user confirming whether the compliance has been satisfied.

The tourniquet further includes a second sensor connected to the controller. The second sensor is configured to output a second signal when the strap is tensioned relative to the buckle housing. The processor is further configured to execute a second determining task that determines whether the strap is tensioned relative to the buckle housing based on whether the second signal is received.

The first sensor is configured to output a third signal that is different from the first signal (i.e., does not output the first signal) when the clasp is not inserted into the receptacle. The first determining task determines that the clasp is removed from the receptacle when either the third signal is received or the first signal is not received from the first sensor, after the first determining task has determined that the clasp has been inserted. The third signal can be no signal.

The processor is further configured to execute a third determining task that determines whether the compliance has been satisfied. The third determining task determines that the compliance has been satisfied when the first determining task determines that the claps is removed within a first predetermined period after the first determining task determined that the clasp has been inserted.

The processor is further configured to execute a second communication task that controls the first communication interface to transmit a successful compliance signal to the external communication apparatus upon the third determining task determining that the compliance has been satisfied.

The processor is further configured to execute a third communication task that receives a logging confirmation signal from the external communication apparatus after sending the successful compliance signal to the external communication apparatus.

The alerting task controls the indicator to alert the user confirming that the compliance has been satisfied when the third determining task determines that the compliance has been satisfied. The alerting task can also control the indicator to alert the user that the compliance has not been satisfied when the third determining task determines that the compliance has not been satisfied within the first predetermined period after the first determining task has determined that the clasp has been inserted. Alternatively, the alerting task can control the indicator to alert the user that the compliance has not been satisfied when the second determining task determines that the strap is not tensioned within the first predetermined period after the first determining task determined that the clasp has been inserted.

The alerting task controls the indicator to alert the user confirming a successful compliance logging upon the third communication task receiving the logging confirmation signal from the external communication apparatus. The alerting task also can control the indicator to alert the user that the logging was not successful when the third communication task does not receive the logging confirmation signal from the external communication apparatus with a predetermined period.

The tourniquet can include a second communication interface that communicates with the external communication apparatus. The first communication interface can use a wireless protocol to communicate with the external communication apparatus, and the second communication interface can use a wired connection protocol to communicate with the external communication apparatus.

The indicator can be a single LED (or multiple LEDs) having at least two different color scheme to indicate different statuses using different colors.

Another aspect is a method of determining whether a compliance has been satisfied using the tourniquet. The method can include a first determining step of determining whether the clasp has been inserted in the receptacle based on the first signal, a first communication step of controlling the first communication interface to initiate communication with the external communication apparatus upon the first determining step determining that the clasp has been inserted, and an alerting step of controlling the indicator to alert a user confirming whether the compliance has been satisfied.

Another aspect is a system for communicating compliance. The system can include the tourniquet and the external communication apparatus. The external communication apparatus is communicable with at least one of an insurance provider, health insurance provider, or medicine provider, via the Internet.

BRIEF DESCRIPTION OF THE DRAWINGS

FIGS. 12A-12C illustrate logical flow charts of the CPU operation according to the present invention.

DETAILED DESCRIPTION

FIGS. 1A-4 illustrate a conventional blood constricting apparatus TQ, in particular, TECH-MED or POZITEEV tourniquet available at AMAZON (http://www.amazon.com/Tech-85954-Quick-Release-Tourniquet/dp/B002BTVS9A/ref=sr_1_1?ie=UTF8&qid=1457124862&sr=8-1&keywords=tech-med+tourniquet or http://www.amazon.com/Poziteev-2-Pack-Tourniquet/dp/B00ZISQYI6/ref=pd_sim_328_1?ie=UTF8&dpID=41N9vgOxzqL&dpSrc=sims&preST=_AC_UL160_SR160%2C160_&refRID=0R2P092B0P4YT6C60690).

The tourniquet TQ comprises an elastic strap S, a buckle B, a clasp C attached to one end of the strap S, and a clasp-receiving receptacle (hereafter "receptacle") R configured to receive the clasp C and lock the same to the receptacle R, which is pivotally mounted to the housing Hb of the buckle B via a pivot pin P. The buckle housing Hb is configured to permit the strap S to slide through when unlocked. The clasp C, the receptacle R, and the housing Hb are configured to lock the strap in place when tension is applied to the strap. These components provide a latching/strap retention mechanism. In particular, the tourniquet TQ uses a "quick release" or "quick slow release" mechanism with a friction/clamp mechanism to maintain the strap in tension.

Figure 1A:
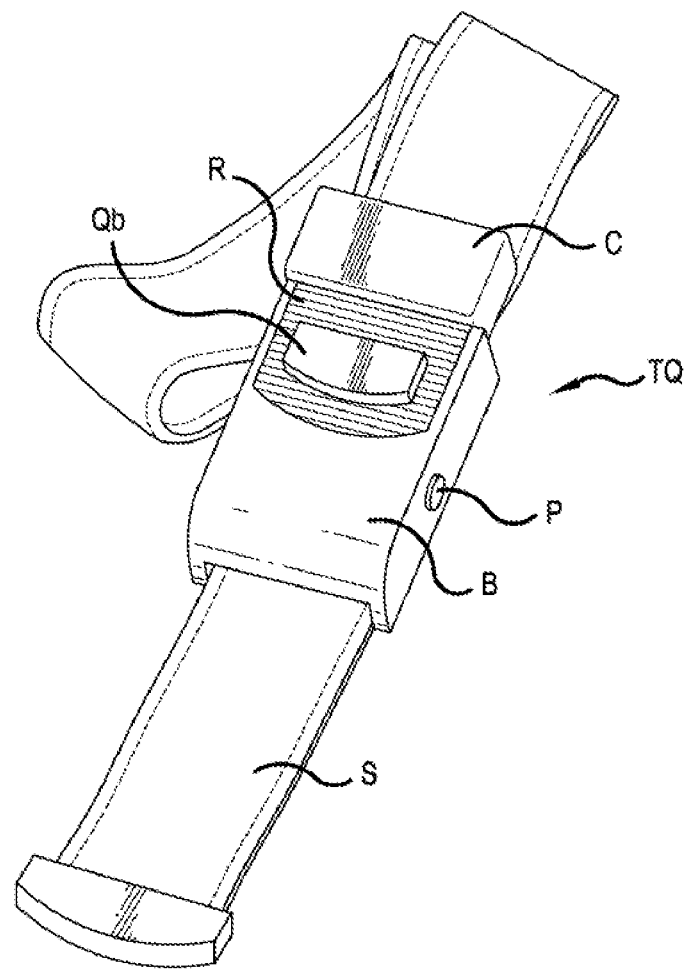
FIGS. 1A-1B schematically illustrate a conventional tourniquet, FIG. 1A illustrating a front perspective view thereof and FIG. 1B illustrating a rear perspective view thereof.
Figure 1B:
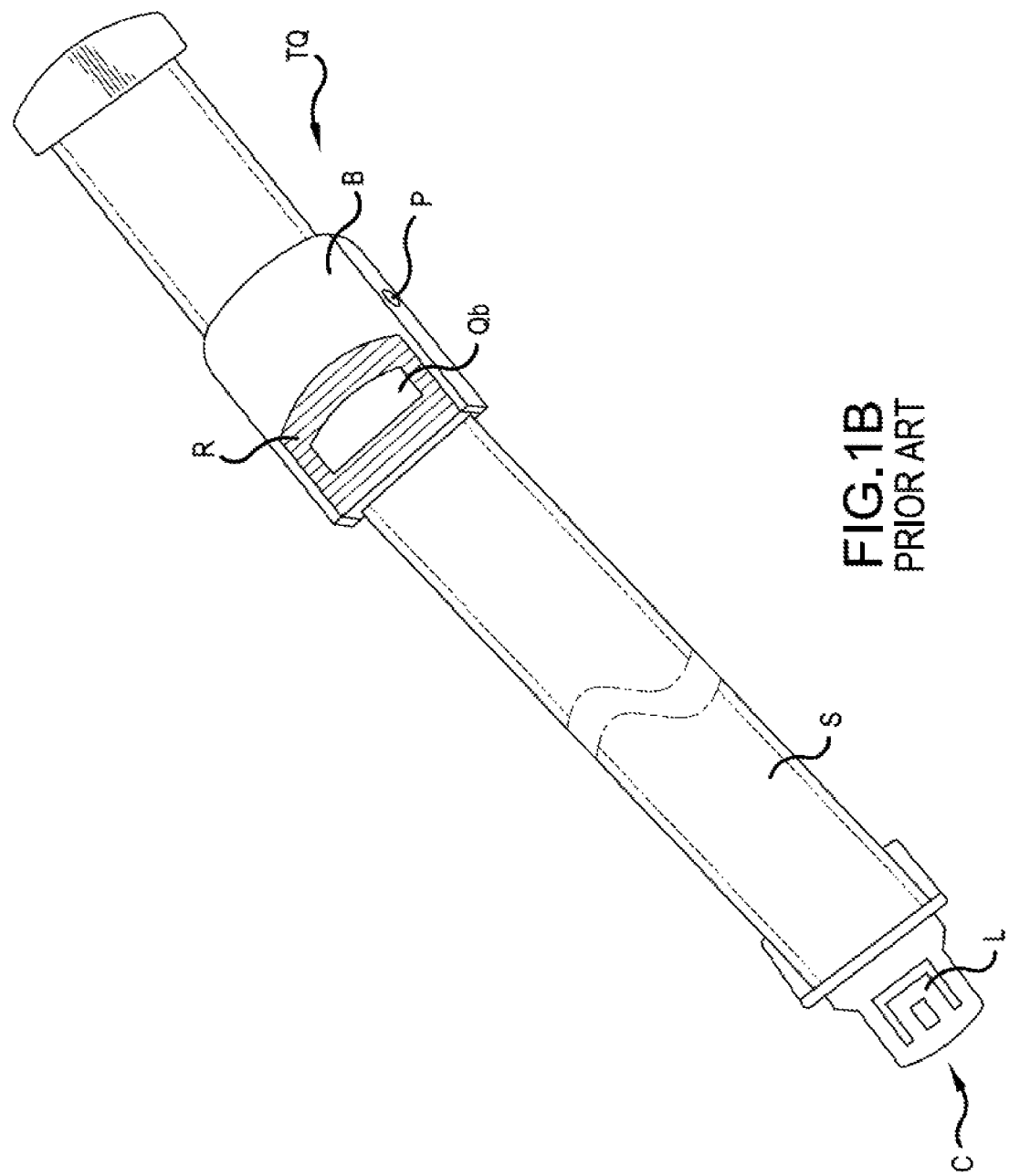
Figure 2:
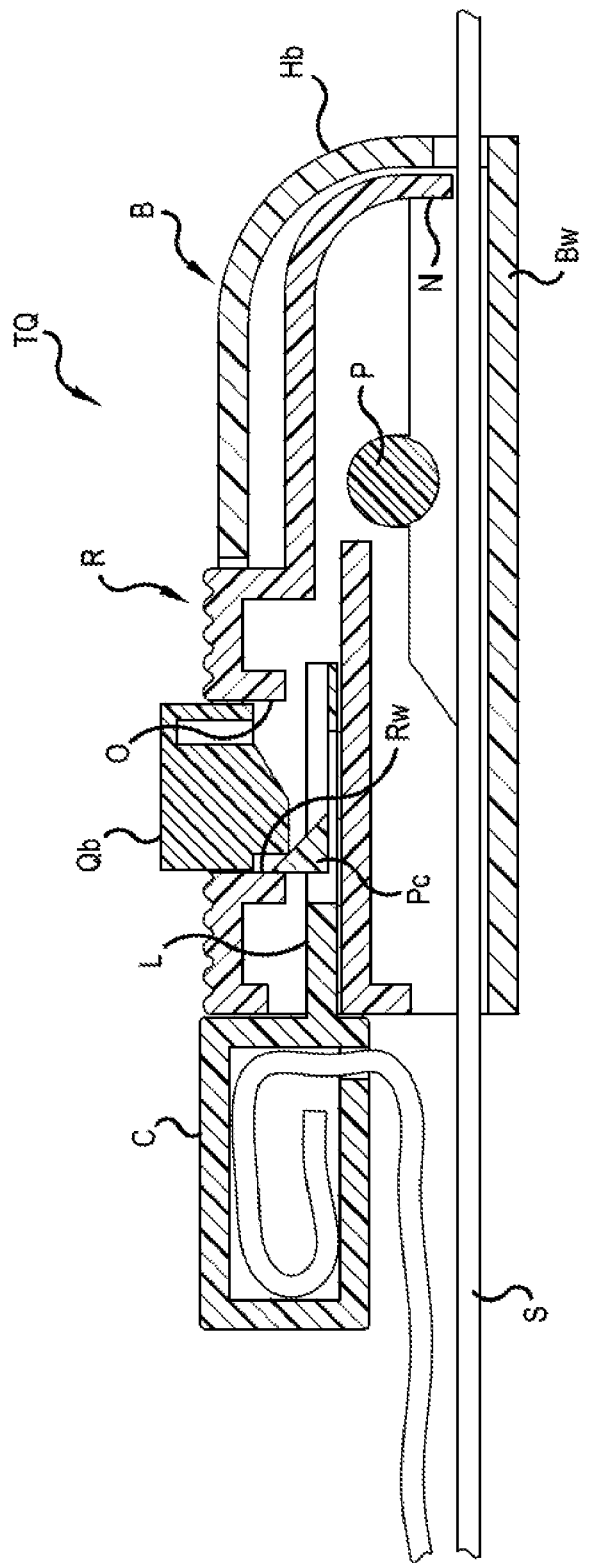
FIG. 2 illustrates a longitudinal cross-sectional view of the embodiment illustrated in FIGS. 1A-1B showing a clasp thereof fully inserted and locked into a clasp-receiving receptacle thereof.
Figure 3:
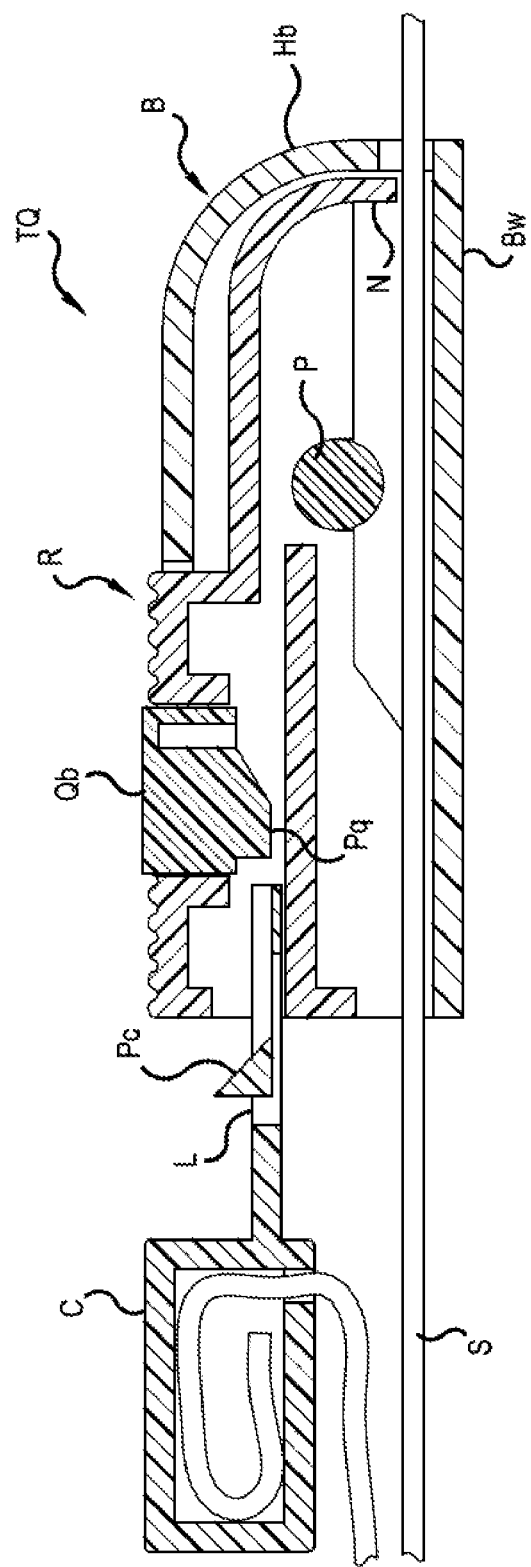
FIG. 3 is similar to FIG. 2, but with the clasp withdrawn from the buckle.
Figure 4:
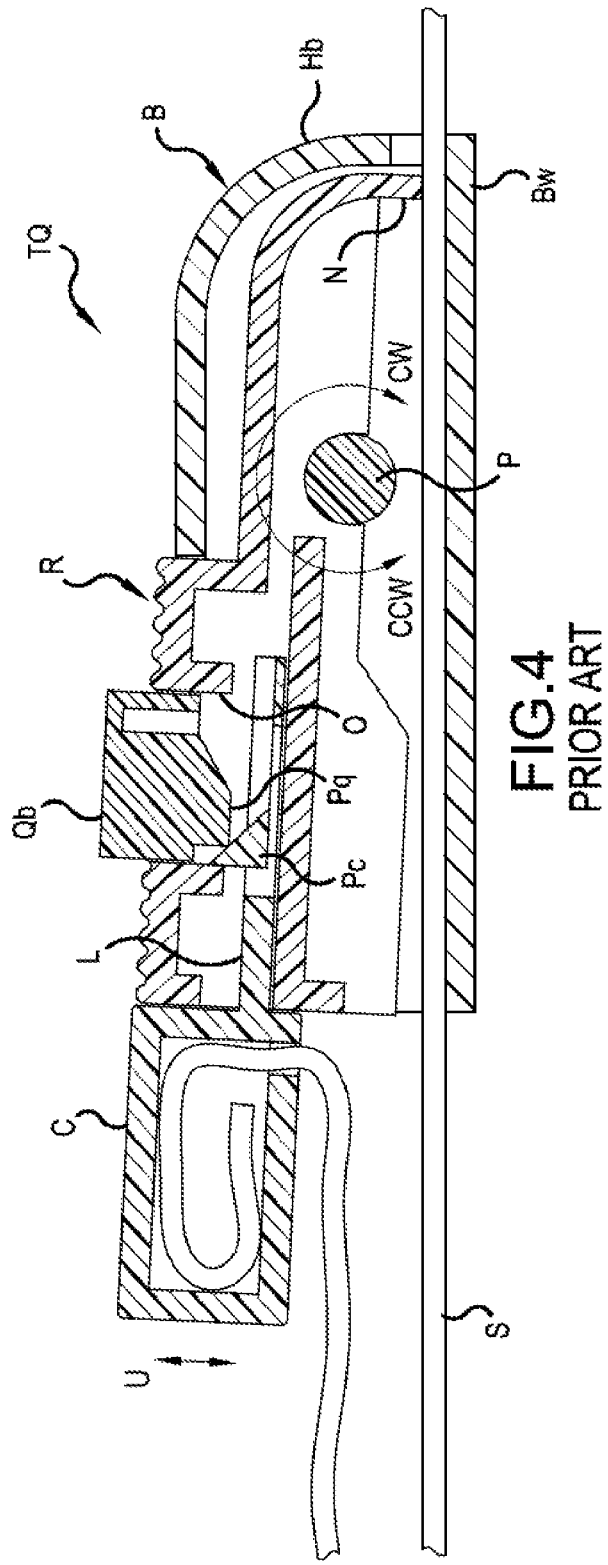
FIG. 4 is similar to FIG. 2, but illustrates the situation when a strap thereof applies tension to the clasp-receiving receptacle, namely when the strap is pulled to the right to apply pressure, causing it to pivot clockwise to lock the strap.

Specifically, referring to FIGS. 2-4, a slot/gap is provided in the buckle housing Hb to permit the strap S to slide across, allowing the user to tension the strap. Referring to FIG. 4, the stretch quality of the elastic strap creates a pressure-friction to keep the strap in place. That is, when the strap S is tensioned (the strap S is not shown in tension in FIGS. 2-4) during use and thus made taut while the elastic strap is wrapped around, for instance a person's arm, the receptacle R pivots about the pivot pin P (clockwise CW in FIG. 4), causing a nose end portion N to pinch the strap S against a bottom wall Bw of the buckle housing Hb, to prevent the strap S from sliding relative to the buckle B.

Referring to FIGS. 2-3, when no tension is applied to the strap S or the clasp C is not inserted into the receptacle R, the receptacle is freely pivotable about the pivot pin P (in the CW or CCW direction in FIG. 4) to allow the strap S to slide across the gap provided between the receptacle's nose end portion N and the bottom wall Bw of the buckle housing Hb. But when the clasp C is inserted and tension is applied to the strap S, the tension causes the clasp C to move upwardly U in FIG. 4, causing the receptacle R to pivot clockwise CW relative to the buckle, which causes the nose end portion N to cinch/clamp on the strap against the bottom wall Bw, locking the strap S relative to the buckle B.

FIG. 2 shows the clasp C inserted into the receptacle R. The clasp C has a latching mechanism that allows the clasp C to enter through a slot in the receptacle R but prevents the clasp C from being pulled out when the strap is pulled to allow the one end of the strap S to be secured relative to the buckle B. Specifically, the clasp C has a U-shaped latch L (see FIG. 1B) that extends inwardly from the distal (free) end toward the strap. The end of the latch is provided with an upwardly and laterally extending prong Pc that is configured to be engageable with a protruding part Pq, namely the bottom of a quick-release button Qb. The latch L is configured to flex to bias the prong to engage against the wall Rw of the opening provided in the receptacle R. The quick-release button extends outwardly (upwardly) through the opening O (see FIGS. 2-4) provided in the receptacle R when the clasp C is inserted into the receptacle R.

As the clasp C is being inserted into the receptacle, the prong Pc engages and slides on the upper wall surface of the receptacle R, which causes the latch L to flex. It remains in the flexed state until it reaches the opening O where it flexes back to the default (unstressed) state and engages the wall Rw (see FIG. 2) in the opening O, preventing the clasp C from being pulled out from the receptacle. As the prong Pc enters the opening O, it engages the protruding part Pq (the bottom the quick-release button Qb), causing it to lift so that part thereof protrudes upwardly as shown in FIGS. 2 and 4. The quick-release button Qb is disposed in the opening O and is freely movable up and down.

When the clasp C is inserted in the receptacle R, the prong Pc urges the quick-release button Qb in the upward position as shown in FIGS. 2 and 4. Pushing down the quick-release button Qb causes the protruding part Pq to be push down on the prong Pc and flexing the latch, expelling the prong Pc out from the opening O to allow the clasp C to be pull out from the receptacle R. When the clasp C is inserted and tension is applied to the strap S during use, pushing the quick-release button Qb causes the clasp C to be released and pulled out from the receptacle due to the tension in the strap S.

The present development can incorporate any conventional strap retention and release mechanism. For illustration purposes, the present embodiment is illustrated using the same latching/strap retention mechanism illustrated in FIGS. 1A-4. That is, referring to FIG. 5, the illustrated tourniquet TQ1 includes the same latching/strap retention mechanisms illustrated in FIGS. 1A-4. Identical components have been identified with the same references and modified components are identified with the same references followed by numeral "1". Since the quick-release and strap retention mechanism operate in the same manner as explained in FIGS. 1A-4, they are not separately explained in details.

Specifically, the present tourniquet TQ1 includes an elastic strap S1, a buckle B1, a clasp C1 attached to one end of the strap S1, and a clasp-receiving receptacle (hereafter "receptacle") R1 configured to receive the clasp C1 and lock the same to the receptacle R1, which is pivotally mounted to the housing Hb1 of the buckle B1 via a pivot pin P. The nose end portion N1 provides the same function as the nose end portion N described previously. The clasp C1 and the receptacle R1 provide the same latching/strap retention mechanism described above with respect to FIGS. 1A-4.

Figure 5:
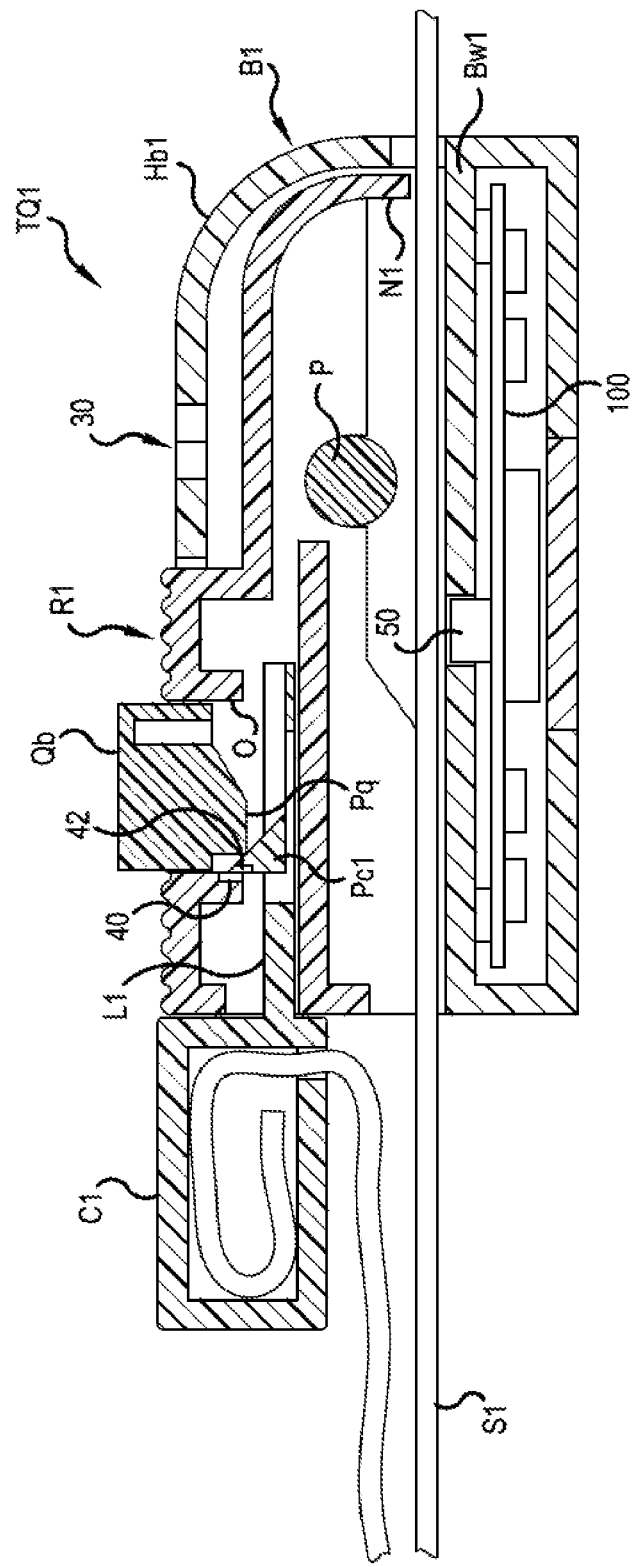
FIG. 5 is a longitudinal cross-sectional view of an embodiment of a tourniquet according to the present invention.
Figure 11:
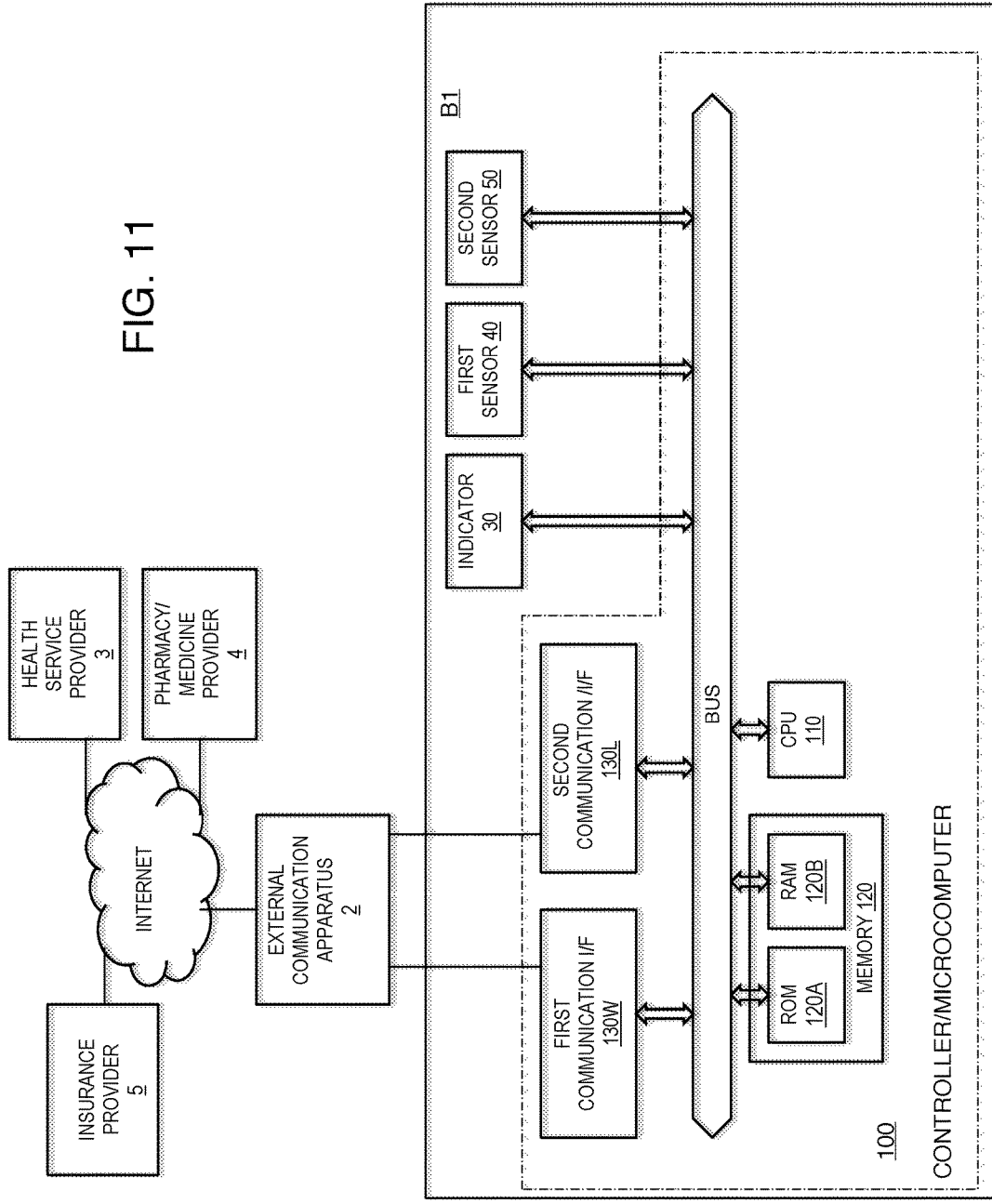
FIG. 11 schematically illustrates a controller or computer provided in the tourniquet illustrated in FIG. 5.

Referring to FIGS. 5 and 11, the present tourniquet TQ1 further includes a controller/microcomputer 100 (and power supply, namely a battery) housed in the buckle B1, an indicator 30, and sensors 30, 40. The buckle housing Hb1 is configured to provide sufficient space to accommodate the controller 100, the indicator 30, and the sensors 30, 40, in addition to the latch and strap retention mechanism described in reference to FIGS. 1A-4. Moreover, the controller/microcomputer 100 includes at least one communication interface 130L or 130W for a 2-way communication between the tourniquet TQ1 and an external communication apparatus 2 to notify whenever the tourniquet TQ1 is being used, for logging purposes.

The present tourniquet TQ1 is unique it that it can communicate with an external apparatus, which marries the two segregated steps, reducing the barrier to compliance. By building the process of logging directly into the process of infusing, the present development can solve the compliance problem, chiefly by reducing from two steps to one. Increased compliance leads to better health outcomes for patients, more accurate data collection for regimen analysis by clinicians, and effective cost-savings for insurance companies. Simply put, the present development is designed to improve the lives of patients, increase the accuracy of clinical analysis, and reduce the cost of people with hemophilia.

Referring to FIG. 11, the controller 100, which is housed inside the buckle B1 includes a processor (CPU) 110 and a memory 120 connected to the processor 110 via a bus. The memory 120 can be a RAM 120A & a ROM 120B. Alternatively, the memory can be a non-volatile computer storage medium, such as a flash memory, instead of the RAM and the ROM, which can be removable, such as using a conventional flash card.

The communication interface includes a first (wireless) communication control circuit (hereafter interface I/F) 130W (communicates with the CPU via a bus) for communicating with the external communication apparatus 2. The first communication I/F 130W can be configured to operate wirelessly, such as using BLUETOOTH or near field communication (NFC), to facilitate communication with a near by external communication apparatus 2 for the express purposes of logging the activation of the tourniquet during an infusion or transfusion. The communication interface also can include a second (wired) communication control circuit (hereafter I/F) 130L (communicates with the CPU via the bus) for communicating with the external communication apparatus 2, such as using conventional USB technology. In this instance, a hardwire would be connected between the second communication I/F 130L and the second communication apparatus 2. The USB technology also can be used to charge the battery (power supply) contained in the buckle.

The external communication apparatus 2 can be a mobile phone, a tablet, such as an IPAD, a laptop computer, or even a basic PC, equipped with BLUETOOTH, NFC, or USB. The external communication apparatus 2 also can be a simple USB network adapter, whether wireless or wired, that allows communication with the Internet.

Figure 9:
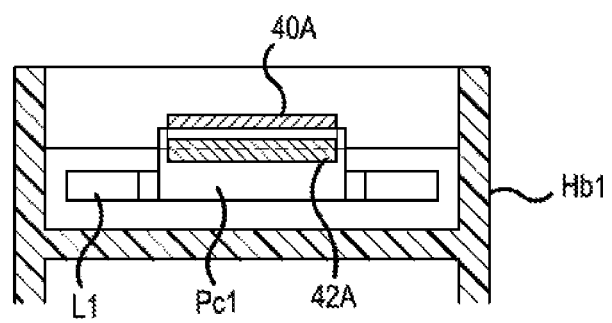
FIG. 9 illustrates a cross-sectional view of the clasp showing a sensor thereof that can detect the clasp being locked to the clasp-receiving receptacle.
Figure 10:
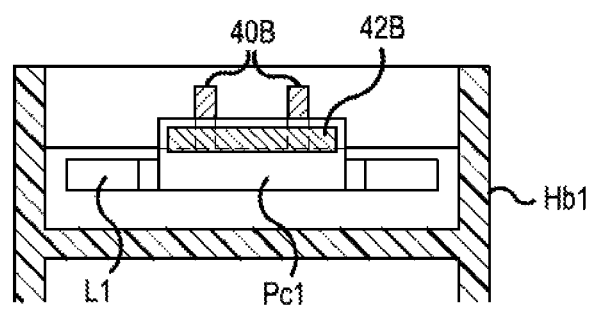
FIG. 10 is similar to FIG. 9 but showing another embodiment of the sensor that can detect the clasp being locked to the claps-receiving receptacle.

Referring to FIGS. 5, 9, and 10 a first switch/sensor 40A, 40B (hereafter "first sensor 40") is disposed in the receptacle R1 in association with a triggering element 42A, 42B (generically identified as 42 in FIG. 5) disposed at a prong Pc1 of a latch L1 so that when the clasp C1 is inserted and locked onto the receptacle R1, the first sensor 40 outputs an engaged (first) signal, which can be an ON signal when the default position of the first sensor 40 outputs an OFF or no signal (or can output OFF or no signal) when the default position of the first sensor 40 outputs an ON signal. Based on the first signal from the first sensor 40, the processor 110 determines whether the clasp is secured to the buckle.

Referring to FIG. 9, the first sensor 40 can be a magnet sensor 40A that is magnetically triggered. Specifically, the first sensor 40A can be disposed facing the opening O of the receptacle R1. The prong Pc1 can include a magnet strip 42A disposed at the surface that makes contact with the wall of the opening O. When the clasp C1 is inserted and the prong Pc1 engages the wall Rw of the opening O, the first sensor 40 can initiate Trigger 1 described later. Alternatively, the first sensor 40 can be a pressure sensor that can be triggered by pressure. For instance, the surface of the prong Pc1 that makes contact with the wall Rw of the opening O can have a protrusion or spring biased element that presses against the first sensor 40 when the clasp is locked to the receptacle R1.

Referring to FIG. 10, first sensor 40 can be a simple pair of spaced electrodes 40B that closes an electrical circuit to initiate Trigger 1 described later. Specifically, the electrodes 40B can be disposed facing the opening O of the receptacle R1. The triggering element in the prong Pc1 can be a conductive strip configured to electrical contact the pair of electrodes 40B when the clasp C1 is locked to the receptacle R1, closing the circuit to initiate Trigger 1.

The communication between the tourniquet TQ1 and the external communication apparatus 2 can be triggered when the processor 110 determines that the clasp C1 is secured to the buckle B1. Specifically, when the clasp C1 is inserted into the receptacle R1, the controller controls the first communication I/F 130W (the external communication having been already paired with BLUETOOTH or NFC or causes to trigger pairing if not paired) to send an initiation signal to the external communication apparatus 2, which upon receiving the initiation signal, triggers the initiation of a preset data log entry reflecting the user's intended medical practice.

The same can be applied when communicating with the second communication I/F 130L, namely USB, with the external communication apparatus 2. In each instance, the external communication apparatus 2 also can interact with at least one of the health service provider 3, pharmacy/medicine provider 5, or insurance provider 5.

After the clasp C1 has been inserted into the receptacle R1, the user tightens the strap S1, for instance around his/her arm, by pulling the strap S1. This cause the second switch/sensor 50 (hereafter "second sensor") to send a strap tensioned (second) signal, which also can be ON (or OFF) signal similarly described with respect to the first sensor 40, to the processor 110, which is an indicia that the user is actually using the tourniquet 101. When the user is finished with the infusion/transfusion, he/she releases the strap S1, and thereafter releases the clasp C1 from the buckle B1 by pressing the quick-release button Qb. As the first sensor 40 is no longer triggered, it no longer outputs the first signal, or outputs no signal or a third signal, indicative of no clasp C1 inserted into the receptacle, to the processor 110.

Figure 6:
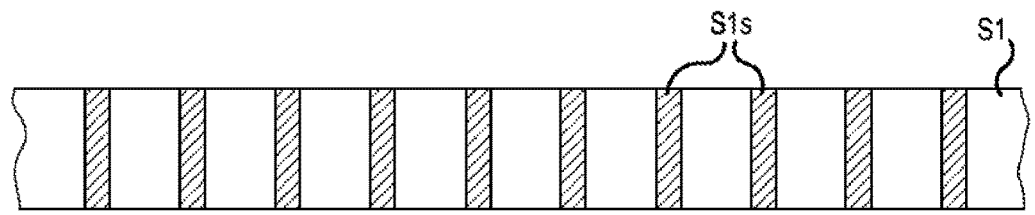
FIG. 6 illustrates a bottom view of the strap illustrated in the embodiment of FIG. 5.

Referring to FIG. 5-6, the strap S1 and the second sensor 50 provide a triggering mechanism that indicates whether the strap S1 is being tensioned. Specifically, the strap S1 can have a stripe configuration where spaced sensor-triggering strip elements S1s are embedded along the length of the strap S1. The strip elements S1e can be magnetic (or magnetically attracted) or light reflective to permit the second sensor 50 disposed adjacent thereto to sense the strap S1 moving relative to the bottom wall Bw1 of the buckle housing Hb1. The strip elements S1s each would trigger a signal whenever they come into contact with or moves across the second sensor 50, which can be magnetically trigger or light triggered sensor. The strip elements S1e can produce successive signals (within some predetermined period) as they move across the second sensor 50, evidencing tightening of the strap S1.

Figure 7:
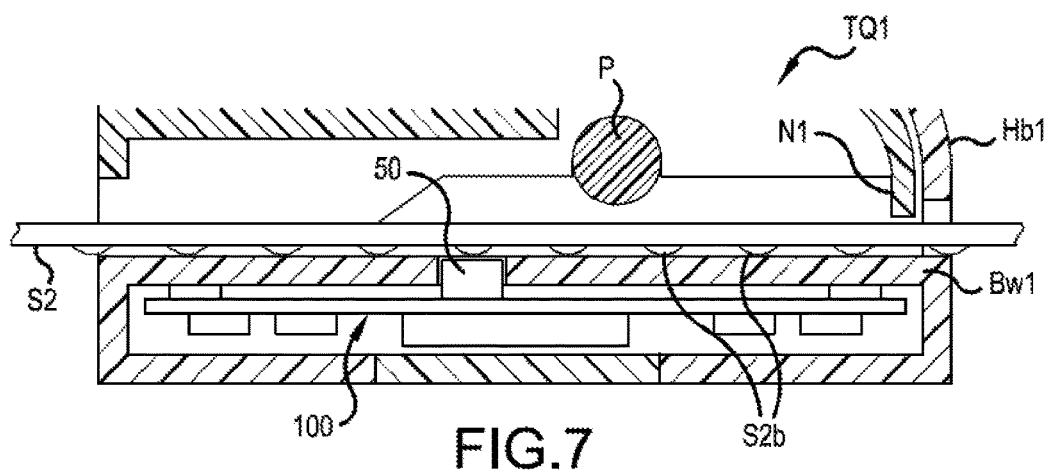
FIG. 7 partially shows the embodiment of FIG. 5 with an alternative embodiment of the strap having bumpers.
Figure 8:
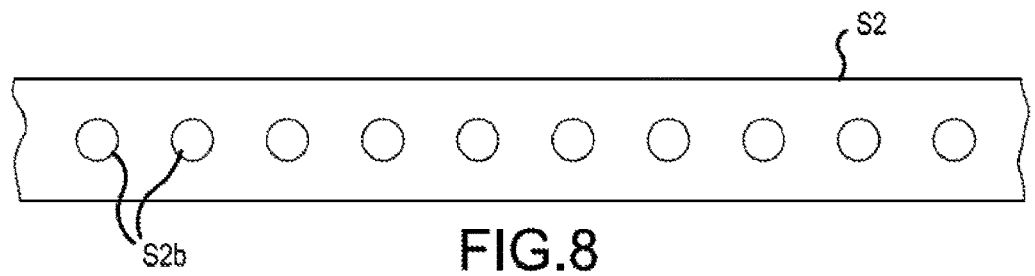
FIG. 8 illustrates the bottom view of the strap of FIG. 7.

Alternatively, referring to FIGS. 7-8, an alternative embodiment of strap S2 can use spaced bumps s2b that protrude outwardly (downwardly in relation to the drawings). As the strap S2 is tightened, the bumps S2b move across the second sensor 50, either contacting or being closely adjacent to the second sensor 50. Like the elements S1s, the bumps S2b can produce successive signals as they move across the second sensor 50. This evidences tensioning the strap S2 to apply pressure. The second sensor 50 can be a contact switch actuated by the bumps SBb contacting or pressing of the sensor 50. Bumps also can be magnetic or light modifying elements similar to the embodiment of FIGS. 5-6.

Alternatively, the second sensor 50 can be composed of first and second contact elements. One of the contact elements can be configured as a sleeve that is concentrically disposed with the pivot pin P and axially spaced from the other contact element fixedly disposed on the pivot pin. The first contact element can be axially movable along the pivot pin as the strap is being tightened (sleeve rolling in one particular direction). The sleeve can be configured as an elongated inner cylinder member and an outer cylindrical member made of a coil spring and disposed concentrically around the cylinder member. The second contact element can be disposed so that it does not move in the axial direction when the sleeve rotates in the one direction. The first contact element, on the other hand, moves axially toward the second contact element as the strap is tightened. The spring is wound in the direction that would cause the spring to compress as the sleeve rotates in the one direction (that causes the constriction to occur), which causes the first contact element to axially move toward the second contact element to actuate the second sensor 50. Releasing the strap tension releases the spring tension causing the first contact element to move away from the second contact element to the default (standby) position at which the strap does not apply any tension.

Alternatively, the second sensor 50 can be a pair of spring loaded switches placed adjacent to where the ends of the pivot pin are mounted to the buckle housing. For example, the buckle housing Hb1 can have pivot pin supports that have opposing slots that rotatably and slideably support the pivot pin P. As tension is applied to the strap, the pivot pin can slide/move toward the pair of spring loaded switches that can be pushed. Both switches being actuated (pushed) indicates appropriate pressure being applied to the strap. The pivot pin can be biased so that it moves away from the switches.

The processor 110 can determine whether the compliance has been satisfied when certain conditions are met, which can be determined using the first and second sensors 40, 50. For example, after the processor 110 receives the first signal indicative of the clasp C1 being inserted from the first sensor 40, when the processor 110 receives the second signal from the second sensor 50 indicative of the strap being tensioned, followed by receiving either no first signal or the third signal from the first sensor 40, indicative of the clasp C1 having been released, within a predetermined time, for instance 5 minutes, from the time the second signal from the second sensor 50 has been received, the processor 110 determines that the compliance has been satisfied, and cause either the first communication I/F 130W or the second communication I/F 130L to send a successful compliance signal to the external communication apparatus 2.

The external communication apparatus 2 can be preconfigured so that upon receiving the successful compliance signal from either the first or second communication I/F 130W, 130L, it automatically communicates with the at least one of the health service provider 3, pharmacy/medicine provider 5, or insurance provider 5, which handles logging of the patient's compliance. Upon the responding provider successfully logging the compliance, it sends a logging confirmation signal to the external communication apparatus 2, which in turn transmits a logging confirmation signal to the respective first or second communication I/F 130W, 130L, which communicates it to the tourniquet TQ1, indicating a successful data logging.

After receiving a log confirmation signal from the external communication apparatus 2, the processor 110 controls the indicator 30, which can be a visual indicator, such as an LED light, to indicate a successful logging to the user. If the indicator 30 fails to light (in case of LED light), this alerts the user that the expected data log entry has not been correctly loaded/entered, and that he/she must manually check the external communication apparatus 2 and/or manually log using the external communication apparatus (or log onto the respective provider's website), or wait for the tourniquet 10 to automatically upload at a later time. Alternatively, the indicator 30 can include an LED light that provides multiple colors, such as green and red. The processor 110 can control the LED to light green when successfully logged of compliance or red when it fails to log or when successfully logged of non-compliance.

The present development merges infusing and logging so that logging is built directly into the infusing process. To ensure against a false compliance reporting, the present development uses four triggering mechanisms:

Trigger 1: confirmation of clasp TQ1 secured to the buckle B1 (using first sensor 40);
Trigger 2: confirmation of strap tension (using second sensor 50);
Trigger 3: confirmation of clasp TQ1 release (using first sensor 40); and
Trigger 4: confirmation of Trigger 2-3 (or alternatively Trigger 1-2) occurring within a preset time Tp1 after Trigger 1 confirmation.

The four-step check covers the process of infusing from start to finish to protect against false reporting. The memory 120 can store the log of the time/date of triggering of Triggers 1-4. When the external communication apparatus 2 is not available, the tourniquet TQ1 still can be used. When the external communication apparatus becomes available, such as when BLUETOOTH or NFC is successfully paired, or when connected thereto via USB, either the wireless communication control I/F 130W or the communication control I/F 130L can send the stored information or only the successful compliance to the external apparatus 2. When the successful compliance is sent to the external apparatus, upon receiving the confirmation signal from the external apparatus, the processor 110 controls the indicator 30 as previously explained. When the logging is made while the external communication apparatus is not available, upon the processor 110 confirming Trigger 4, it can control the indicator 30 as previously explained.

Figure 12A:
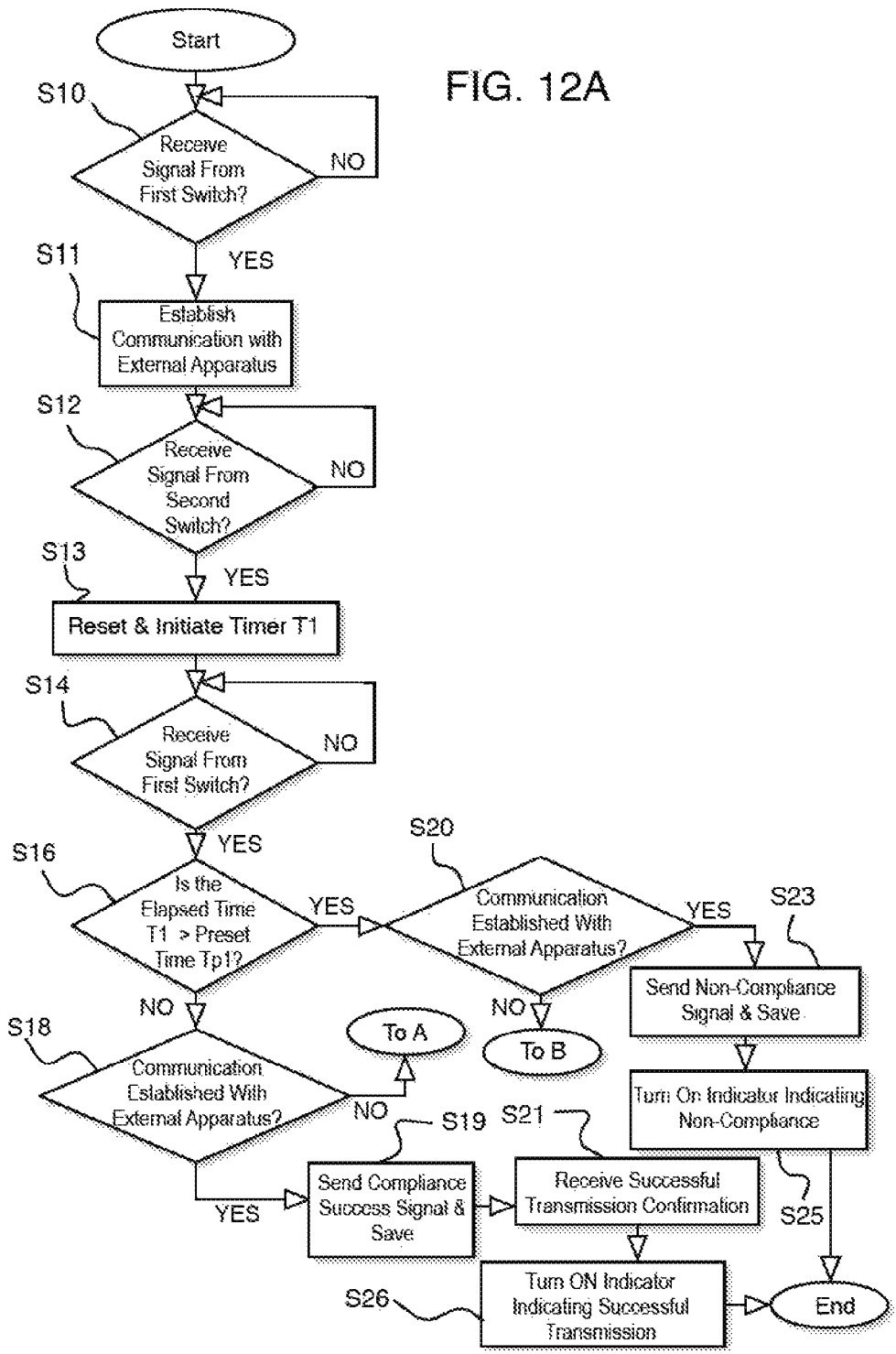
Figure 12B:
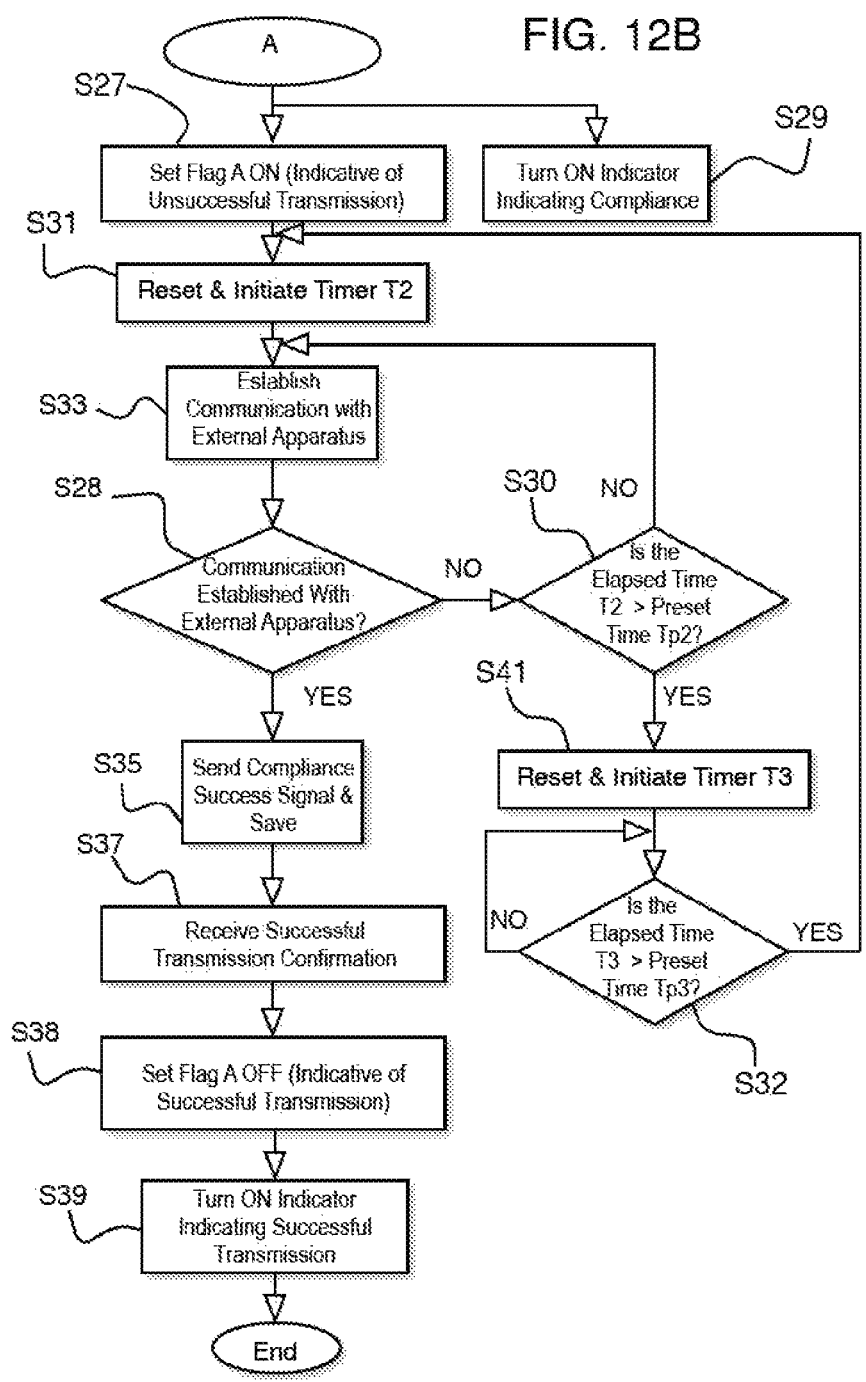

The processor 110 can be programmed to execute the following tasks/steps illustrated in FIG. 12A-12C. Referring to FIG. 12A, the processor 110 executes a first determining task/step in S10 to determine whether the clasp C1 has been inserted in the receptacle R1 based the first signal (indicative of the clasp engaging the buckle) output from the first sensor 40. Specifically, the processor 110 determines whether the first sensor 40 outputs or is outputting the first signal. If negative (NO in S10), the processor 110 again executes the first determining task/step in S10 and repeats in a loop until the processor 110 determines that the first sensor 40 outputs or outputting the first signal (YES in S10). The processor 110 then executes a first communication task/step in S11 that controls either the first or second communication I/F 130L or 130W to initiate or establish communication with the external apparatus 2. Specifically, the processor 110 can control the first or second communication I/F to transmit an initiating signal to the external communication apparatus 2 in S11. The communication task/step in S11 can be automatically achieved when the wired connection is made or when the tourniquet TQ is within a range of wireless communication with the external apparatus 2, or by contacting therewith if provided with an NFC.

The processor 110 thereafter executes a second determining task/step in S12 to determine whether the strap is tensioned relative to the buckle housing 22 based on the second signal output from the second sensor 50. Specifically, the processor 110 determines in S12 whether the second sensor 50 outputs or outputting the second signal indicative of the strap being tightened. If negative (NO in S12), the processor 110 again executes the second determination task/step in S12 and repeats in a loop until the processor 110 determines that the second sensor 50 outputs or is outputting the second signal (YES in S12). In S13, the processor 110 executes a first timer task/step that resets and initiate a timer T1. In S14, the first determining task/step determines whether the first sensor 40 is still outputting the first signal or outputs or outputting the third signal (e.g., no signal), indicative of the clasp being released from the buckle. If negative (NO in S14), the processor 110 again executes the first determining task/step in S14 and repeats in a loop until the processor 110 determines that the first sensor 40 outputs or is outputting the third signal or no longer outputting the first signal (YES in S14).

In S16, the processor 110 executes a third determining task/step that determines whether the compliance has been satisfied. Specifically, the third determining task/step determines that the compliance has been satisfied when the first determining task in S14 determines that the claps is removed, within a first predetermined period Tp1 after the first determining task has determined that the clasp has been inserted in S16. Here, the processor 110 compares the elapsed time T1 with a preset time Tp1 (e.g., 5 minutes), which can be manually set. If the elapsed time T1 is not greater than the preset time Tp1 (NO in S16), the processor 110 executes a communication determining task/step in S18 that determines whether communication has been established with the external apparatus 2. If negative (NO in S18), the processor 110 executes routine A (FIG. 12B). If affirmative (YES in S18), the processor 110 executes a second communication task/step that controls the first or second communication I/F to transmit a successful compliance signal to the external communication apparatus 2 upon the third determining task/step S16 determining that the compliance has been satisfied. Specifically, the processor 110 controls the first or second communication I/F to transmit a compliance success signal to the external apparatus 2 and saves/logs the communication sent thereto in S19.

In an alternative embodiment, the processor 110 can execute the first timer task/step that resets and initiate a timer T1 (i.e., S13) immediately after YES in S10 to keep track of time T1 between receiving the first signal and the second signal instead of keeping track of time between receiving the second signal in S12 and no first signal or third signal in S16.

Here, the processor 110 determines whether the strap is tensioned within the first predetermined period T1 after determining that the clasp has been inserted in S10.

In S21, the processor 110 executes a third communication task/step that determines whether a successful logging confirmation signal from the external communication apparatus 2 has been received. Upon receiving the successful logging confirmation signal from the external communication apparatus 2 within a predetermined time (which can be set in advance by the user), the processor 110 executes an alerting task/step in S26 that controls the indicator 30 to alert the user confirming that the compliance has been satisfied (when the third determining task/step determines that the compliance has been satisfied in (NO in S16). That is, the processor 110 turns ON the indicator 30 indicative of the successful transmission of compliance in S26. For example, the indicator 30 can have multicolor scheme, where a solid color green can indicate successful transmission of compliance, a blinking color green can indicate compliance successful but the transmission not successful, a solid color red can indicate successful transmission of non-compliance, and a blinking color red can indicate unsuccessful transmission of non-compliance. After turning ON the indicator for predetermined time (e.g., 30 seconds), the routine can end.

In S16, when the processor 110 determines that the elapsed time T1 is greater than the preset time Tp1 (YES in S16), which indicates non-compliance, the processor 110 executes the communication determining task/step in S20 that determines whether communication has been established with the external apparatus 2. If negative (NO in S20), the processor 110 executes routine B (FIG. 12C). If affirmative (YES in S20), the processor 110 executes a fourth communication task/step in S23 that controls the first or second communication I/F to transmit non-compliance signal to the external communication apparatus 2, upon the third determining task in S16 determining that the compliance has not been satisfied. Specifically, the processor 110 controls the first or second communication I/F to transmit a non-compliance signal to the external communication apparatus 2 and saves/logs the communication sent thereto in S23. In S25, the processor 110 executes the alerting task/step that controls the indicator 30 to turns ON (e.g., solid color red) indicating or indicative of non-compliance, for a predetermined time, which can be the same as or different from compliance successful transmission indicator duration. Thereafter, the routine can end.

In an alternative embodiment, the processor 110 can also execute the third communication task/step that receives a successful logging confirmation signal from the external communication apparatus 2, similar to S21 after S23 and before S25. Upon receiving the successful logging confirmation signal from the external communication apparatus within a predetermined time (which can be set in advance by the user), the processor 110 executes an alerting task/step in S25 that controls the indicator 30 to alert the user confirming that the compliance has been not satisfied when the third determining task/step determines that the compliance has not been satisfied in (NO in S16). Thereafter, the routine ends.

Referring to FIG. 12B, the processor 110 executes the routine A when the communication determining task/step in S18 determines that communication with the external apparatus 2 is not established (NO in S18). Here, the processor 110 sets flag A ON (indicative of unsuccessful transmission of compliance) in S27 and turns ON the indicator 30 (e.g., blinking green) in S29, indicating compliance but unsuccessful transmission, for the predetermined time, which again can be the same as or different from compliance successful transmission indicator duration.

In S31, the processor 110 resets and initiates timer T2. In S33, the processor causes either the first or second communication I/F to establish communication with the external apparatus 2. In this respect, the processor 110 can control the first or second communication I/F to transmit an initiating signal to the external communication apparatus. In S28, the processor 110 determines whether communication with the external apparatus 2 has been established. If affirmative (YES in S28), the processor 110 sends a compliance successful signal to the external apparatus and saves/logs the communication sent thereto in S35. In S38 and S39, upon receiving a successful transmission confirmation signal from the external apparatus 2 within a predetermined time (which can be set in advance by the user) in S37, the processor 110 sets the flag A OFF indicative of successful transmission and turns ON the indicator (e.g., solid green) for the predetermined time, which again can be set by the user, and thereafter can end the routine A.

If negative (NO) in S28, the processor 110 compares the elapsed time T2 with a second preset time Tp2 (e.g., 4 minutes), which can be manually set, in S30. If the elapsed time T2 is not greater than the preset time Tp2 (NO in S30), the processor 110 executes task S33 and repeats in a loop. In S30, when the processor 110 determines that the elapsed time T2 is greater that the preset time Tp2 (YES in S30), the processor resets and initiates timer T3. Thereafter, the processor 110 compares in S32 the elapsed time T3 with a preset time Tp3 (e.g., 4 hours), which can be manually set. When the processor 110 determines that the elapsed time T3 is greater than the preset time Tp3, the processor 110 executes S31. When the processor 110 determines that the elapsed time T3 is not greater than the preset time Tp3 (NO in S32), it waits until the preset time Tp3 lapses. This routine allows the tourniquet to automatically establish communication with the external communication device when the communication later becomes available. That is, S31, S33, and S28 is again executed after the preset time Tp3 expires.

Referring to FIG. 12C, the processor 110 executes the routine B, which is similar to the routine A for unsuccessful communication of non-compliance, when it determines that the communication is not established (NO in S20). The processor 110 sets flag B ON (indicative of unsuccessful transmission of non-compliance) in S43 and turns ON the indicator 30 (e.g., blinking red) in S45, indicating non-compliance and unsuccessful transmission for the predetermined time, which again can be set by the user.

In S47, the processor 110 resets and initiates timer T2. In S49, the processor 110 causes either the first or second communication I/F to establish communication with the external apparatus 2. In this respect, the processor 110 can control the first or second communication I/F to transmit an initiating signal to the external communication apparatus. In S40, the processor 110 determines whether the communication with the external apparatus 2 has been established. If affirmative (YES in S40), the processor 110 sends a non-compliance successful transmission signal to the external apparatus and saves/logs the communication sent thereto in S51. In S54 and S55, upon receiving a successful transmission confirmation signal from the external apparatus 2 within a predetermined time (which can be set in advance by the user) in S53, the processor 110 sets the flag B OFF indicative of successful transmission of non-compliance and turns ON the indicator (e.g., solid red) for the predetermined time, which again can be set by the user, and thereafter can end the routine B.

If negative (NO) in S40, the processor 110 compares the elapsed time T2 with a second preset time Tp2 (e.g., 4 minutes), which can be manually set, in S42. If the elapsed time T2 is not greater than the preset time Tp2 (NO in S42), the processor 110 executes task S49 and repeats in a loop. In S42, when the processor 110 determines that the elapsed time T2 is greater that the preset time Tp2 (YES in S42), the processor resets and initiates the timer T3. Thereafter, the processor 110 compares in S44 the elapsed time T3 with the preset time Tp3 (e.g., 4 hours), which can be manually set. When the processor 110 determines that the elapsed time T3 is greater than the preset time Tp3, the processor 110 executes task S47. When the processor 110 determines that the elapsed time T3 is not greater than the preset time Tp3 (NO in S44), it waits until the preset time Tp3 lapses. This routine allows the tourniquet to automatically establish communication with the external devices when the communication later becomes available, just like S32 in routine A.

The preset times Tp1, Tp2, and Tp3 each are adjustable, namely the user can set the duration.

Given the disclosure of the present invention, one versed in the art would appreciate that there may be other embodiments and modifications within the scope and spirit of the present invention. Accordingly, all modifications attainable by one versed in the art from the present disclosure within the scope and spirit of the present invention are to be included as further embodiments of the present invention. The scope of the present invention accordingly is to be defined as set forth in the appended claims.

What is claimed is:

1. A tourniquet for blood constriction using a strap and a clasp connected to the strap, which is adjustably configured, and communicable with an external communication apparatus configured to transmit a logging confirmation signal to the tourniquet confirming a successful logging of compliance, the tourniquet comprising:
   a controller;
   an indicator connected to the controller;
   a first sensor connected to the controller; and
   a housing containing the controller and the first sensor,
      wherein the housing includes a receptacle configured to receive the clasp,
      wherein the first sensor is configured to output a first signal when the clasp is inserted into the receptacle, and
      wherein the controller comprises:
         a first communication interface configured to communicate with the external communication apparatus;
         a memory; and
         a processor configured to execute:
            a first determining task that determines whether the clasp has been inserted in the receptacle based on whether the first signal is received;
            a first communication task that controls the first communication interface to initiate communication with the external communication apparatus upon the first determining task determining that the clasp has been inserted; and
            an alerting task that controls the indicator to alert a user confirming whether the compliance has been satisfied.

2. The tourniquet according to claim 1, further comprising:
   a second sensor connected to the controller, and configured to output a second signal when the strap is tensioned relative to the buckle housing,
   wherein the processor is further programmed to execute a second determining task that determines whether the strap is tensioned relative to the housing based on whether the second sensor outputs the second signal.

3. The tourniquet according to claim 2, wherein:
   the first sensor is further configured to output a third signal that is different from the first signal when the clasp is not inserted in the receptacle, and
   the first determining task determines that the clasp is removed from the receptacle when either the third signal is received from the first sensor or the first signal is not received from the first sensor, after the first determining task determined that the clasp has been inserted.

4. The tourniquet according to claim 3, wherein:
   the processor is further configured to execute a third determining task that determines whether the compliance has been satisfied,
   the third determining task determines that the compliance has been satisfied when the first determining task determines that the claps is removed within a first predetermined period after the first determining task has determined that the clasp has been inserted.

5. The tourniquet according to claim 4, wherein the alerting task controls the indicator to alert the user confirming that the compliance has been satisfied when the third determining task determines that the compliance has been satisfied.

6. The tourniquet according to claim 5, wherein the alerting task controls the indicator to alert the user that the compliance has not been satisfied when the third determining task determine that the compliance has not been satisfied within the first predetermined period after the first determining task has determined that the clasp has been inserted.

7. The tourniquet according to claim 4, wherein the processor is further configured to execute a second communication task that controls the first communication interface to transmit a successful compliance signal to the external communication apparatus upon the third determining task determining that the compliance has been satisfied.

8. The tourniquet according to claim 7, wherein the processor is further configured to execute a third communication task that receives a logging confirmation signal from the external communication apparatus after sending the successful compliance signal to the external communication apparatus.

9. The tourniquet according to claim 8, wherein the alerting task controls the indicator to alert the user confirming a successful compliance logging upon the third communication task receiving the logging confirmation signal from the external communication apparatus.

10. The tourniquet according to claim 1, wherein the first communication interface uses a wireless protocol to communicate with the external communication apparatus.

11. The tourniquet according to claim 10, further including a second communication interface that communicates with the external communication apparatus using a wired connection protocol.

12. The tourniquet according to claim 1, wherein the indicator comprises an LED or multiple LEDs having at least two different color scheme to indicate different statuses using different colors.

13. A method of determining whether a compliance has been satisfied using a tourniquet for blood constriction that uses a strap and a clasp connected to the strap, which is adjustably configured, and communicable with an external communication apparatus configured to transmit a logging confirmation signal to the tourniquet confirming a successful logging of compliance, wherein the tourniquet comprises:
a controller;
an indicator connected to the controller;
a first sensor connected to the controller; and
a housing containing the controller and the first sensor,
wherein the housing has a receptacle configured to receive the clasp,
wherein the first sensor is configured to output a first signal when the clasp is inserted into the receptacle, and
wherein the controller comprises:
a first communication interface configured to communicate with the external communication apparatus, and connected to the processor;
a memory; and
a processor,
wherein the method is executable by the processor and comprises:
a first determining step of determining whether the clasp has been inserted in the receptacle based on whether the first signal is received;
a first communication step of controlling the first communication interface to initiate communication with the external communication apparatus upon the first determining step determining that the clasp has been inserted; and
an alerting step of controlling the indicator to alert a user confirming whether the compliance has been satisfied.

14. A system for communicating compliance comprising:
a tourniquet for blood constriction that uses a strap and a clasp connected to the strap, which is adjustable; and
an external communication apparatus,
wherein the tourniquet and the external communication apparatus are communicable with each other,
wherein the external communication apparatus is configured to transmit a logging confirmation signal to the tourniquet confirming a successful logging of compliance, and
wherein the tourniquet comprises:
a controller;
an indicator connected to the controller;
a first sensor connected to the controller; and
a housing containing the controller and the first sensor,
wherein the housing has a receptacle configured to receive the clasp,
wherein the first sensor is configured to output a first signal when the clasp is inserted into the receptacle, and
wherein the controller comprises:
a first communication interface configured to communicate with the external communication apparatus;
a memory; and
a processor configured to execute:
a first determining task that determines whether the clasp has been inserted in the receptacle based on whether the first signal is received;
a first communication task that controls the first communication interface to initiate communication with the external communication apparatus upon the first determining task determining that the clasp has been inserted; and
an alerting task that controls the indicator to alert a user confirming whether the compliance has been satisfied.

15. The system according to claim 14, wherein the external apparatus is communicable with at least one of an insurance provider, health insurance provider, or medicine provider via the Internet.

* * * * *

UNITED STATES PATENT AND TRADEMARK OFFICE
CERTIFICATE OF CORRECTION

PATENT NO.        : 10,136,903 B2
APPLICATION NO.   : 15/082865
DATED             : November 27, 2018
INVENTOR(S)       : Patrick James Lynch et al.

Page 1 of 1

It is certified that error appears in the above-identified patent and that said Letters Patent is hereby corrected as shown below:

In the Claims

In Claim 2, Column 13, Line 65, the word "buckle" should be deleted.

Signed and Sealed this
Twenty-ninth Day of October, 2019

Andrei Iancu
*Director of the United States Patent and Trademark Office*

UNITED STATES PATENT AND TRADEMARK OFFICE
CERTIFICATE OF CORRECTION

| | |
|---|---|
| PATENT NO. | : 10,136,903 B2 |
| APPLICATION NO. | : 15/082865 |
| DATED | : November 27, 2018 |
| INVENTOR(S) | : Patrick James Lynch et al. |

It is certified that error appears in the above-identified patent and that said Letters Patent is hereby corrected as shown below:

On the Title Page

Delete Item (73).

Signed and Sealed this
Seventh Day of June, 2022

Katherine Kelly Vidal
*Director of the United States Patent and Trademark Office*